United States Patent
Shah et al.

(10) Patent No.: US 11,940,449 B2
(45) Date of Patent: Mar. 26, 2024

(54) SPECIFIC ANTIGEN SEQUENCES FOR COVID-19 AND METHODS OF USE

(71) Applicant: ID-Fish Technology, Inc., Milpitas, CA (US)

(72) Inventors: Jyotsna S. Shah, Santa Clara, CA (US); Song Liu, San Jose, CA (US); Hari-Hara Potula, San Jose, CA (US); Prerna Bhargava, Sunnyvale, CA (US)

(73) Assignee: ID-Fish Technology, Inc., Milpitas, CA (US)

( * ) Notice: Subject to any disclaimer, the term of this patent is extended or adjusted under 35 U.S.C. 154(b) by 211 days.

(21) Appl. No.: 17/669,979

(22) Filed: Feb. 11, 2022

(65) Prior Publication Data

US 2022/0260586 A1    Aug. 18, 2022

Related U.S. Application Data

(60) Provisional application No. 63/149,998, filed on Feb. 16, 2021.

(51) Int. Cl.
| | |
|---|---|
| A61P 31/14 | (2006.01) |
| A61P 35/00 | (2006.01) |
| A61P 37/04 | (2006.01) |
| C07K 14/005 | (2006.01) |
| C07K 14/165 | (2006.01) |
| C07K 16/10 | (2006.01) |
| G01N 33/68 | (2006.01) |

(52) U.S. Cl.
CPC ....... *G01N 33/6854* (2013.01); *C07K 14/005* (2013.01); *C12N 2770/20022* (2013.01); *G01N 2333/165* (2013.01); *G01N 2469/20* (2013.01); *G01N 2800/26* (2013.01)

(58) Field of Classification Search
CPC ....... G01N 2333/165; G01N 33/56983; G01N 2469/10; G01N 2469/20; G01N 33/6854
See application file for complete search history.

(56) References Cited

FOREIGN PATENT DOCUMENTS

WO    WO2022106860    *    5/2022

OTHER PUBLICATIONS

Liu S. et al., "Pilot Study of Immunoblots with Recombinant Borrelia burgdorferi Antigens for Laboratory Diagnosis of Lyme Disease", Healthcare 6, 99 (2018), 15 pages.
Shah J.S. et al., "Line Immunoblot Assay for Tick-Borne Relapsing Fever and Findings in Patient Sera from Australia, Ukraine and the USA", Healthcare 7(4), 121 (2019), 17 pages.

* cited by examiner

*Primary Examiner* — Barry A Chestnut
(74) *Attorney, Agent, or Firm* — Pierce Atwood LLP

(57) ABSTRACT

Compositions and methods for immunological detection of coronavirus antibodies are provided.

17 Claims, 2 Drawing Sheets
Specification includes a Sequence Listing.

SPECIFIC ANTIGEN SEQUENCES FOR COVID-19 AND METHODS OF USE

RELATED APPLICATIONS

This application claims benefit under 35 U.S.C. § 119(e) of U.S. Provisional application Ser. No. 63/149,998, filed Feb. 16, 2021, the entire contents of which is incorporated by reference herein in its entirety.

SEQUENCE LISTING

The instant application incorporates by reference the Sequence Listing in the ASCII text file filed Feb. 11, 2022, entitled "ID-FISH 0153-2017US02—Sequence Listing_ST25.txt", which was created on Jan. 27, 2022 the size of which file is 20,922 bytes.

FIELD OF THE INVENTION

The invention relates, in part, to novel compositions and methods for detection of coronavirus-specific antibodies.

BACKGROUND OF THE INVENTION

Coronavirus Disease 2019 (COVID-19) is caused by severe acute respiratory syndrome coronavirus 2 (SARS-CoV-2). The SARS-CoV-2 pandemic that originated in Wuhan, China in December, 2019, and then rapidly spread globally is reported to have caused approximately 109 million infections and 2.4 million deaths world-wide as of Feb. 15, 2021 (Coronavirus Resource Centre, coronavirus.jhu.edu/map.html). Major challenges of SARS-CoV-2 for healthcare practitioners, healthcare systems, and public health systems include high infectivity and mortality rates, particularly in individuals of older age and those with pre-existing health conditions, and the fact that COVID-19 affects different persons in different ways. Infected persons have had a wide range of symptoms reported—from mild symptoms to severe illness. COVID-19 symptoms may appear 2-14 days after exposure to the virus, and may mimic, for example, viral flu-like symptoms. Reported COVID-19 symptoms include: fever or chills, cough, shortness of breath or difficulty breathing, low blood oxygen saturation levels, fatigue, muscle or body aches, headache, new loss of taste or smell, sore throat, congestion or runny nose, nausea or vomiting, or diarrhea. Emergency warning signs for COVID-19 include: trouble breathing, persistent pain or pressure in the chest, new confusion and inability to wake or stay awake.

Infection is most commonly diagnosed at present by nucleic acid amplification tests (NAATs), often real-time RT-PCR, performed on nasopharyngeal and mid-turbinate swabs. However, detection of antibodies to SARS-CoV-2 is also important for multiple reasons, including: (i) confirming present or past infection, (ii) evaluating patients with negative NAATs who show characteristic SARS-CoV-2 disease symptoms, (iii) performing sero-epidemiological studies on the disease, (iv) assessing the development of antibody-mediated protective immunity in both individual patients and a population, and (v) investigating immune response and immunopathology during the disease. The spike (S) glycoprotein and nucleocapsid (N) protein of SARS-CoV-2 have been used as target antigens in serological assays. The S protein is exposed on the outside of the virus membrane while N encapsulates viral RNA inside the membrane envelope. S is composed of an N-terminal S1 region containing a receptor binding domain (RBD) which binds to the angiotensin-converting enzyme 2 (ACE2) receptor on host cells, and a C-terminal S2 region that subsequently mediates fusion between the viral and host cell membranes to allow entry of viral RNA into the cell.

An additional challenge for immunological testing for coronaviruses and for SARS-CoV-2 is that different subjects may have different antibody responses, making a positive response difficult to detect with sensitivity and specificity.

SUMMARY

According to an aspect of the invention, a composition is provided, the composition including at least four labelled and/or tagged and/or bound amino acid sequences, wherein the at least four labelled and/or tagged and/or bound amino acid sequences include amino acid sequences SEQ ID NO: 1, SEQ ID NO: 2, SEQ ID NO: 3, and SEQ ID NO: 4, and variants thereof which retain the immunological binding profile of the corresponding non-variant. In some embodiments, the at least four labelled and/or tagged and/or bound amino acid sequences of the composition are bound to a substance selected from the group consisting of nitrocellulose, nylon, polyvinylidene difluoride (PVDF), magnetic beads, and agarose. In some embodiments, the composition also includes at least two labelled and/or tagged and/or bound amino acid sequences, wherein the at least two labelled and or tagged and/or bound amino acid sequences include amino acid sequences SEQ ID NO: 5 and SEQ ID NO: 6, and variants thereof which retain the immunological binding profile of the corresponding non-variant.

According to another aspect of the invention, a method for detecting IgM-class antibodies resulting from infection by a coronavirus, if present in a biological sample obtained from a subject suspected of having a coronavirus infection, is provided, the method including: a) providing a composition including at least four labelled and/or tagged and/or bound amino acid sequences, wherein the at least four labelled and/or tagged and/or bound amino acid sequences include amino acid sequences SEQ ID NO: 1, SEQ ID NO: 2, SEQ ID NO: 3, and SEQ ID NO: 4, and variants thereof which retain the immunological binding profile of the corresponding non-variant; b) providing the biological sample obtained from the subject suspected of having a coronavirus infection; c) contacting the biological sample with the composition of step a) under conditions appropriate for specific antibody binding to an epitope; and d) detecting specific binding of IgM-class antibodies with the amino acid sequences of step a), wherein the sample is scored as positive for coronavirus infection when at least two of the amino acid sequences of step a) exhibit positive binding with IgM-class antibodies from the biological sample. In some embodiments, the binding of IgM-class antibodies is detected through the use of an anti-human IgM antibody linked to a detectable moiety. In some embodiments, the amino acid sequences of step a) also include amino acid sequences SEQ ID NO: 5 and SEQ ID NO: 6 and variants thereof which retain the immunological binding profile of the corresponding non-variant; and wherein the sample is scored as positive for coronavirus infection when at least two of the amino acid sequences of step a) exhibit positive binding with IgM-class antibodies from the biological sample. In certain embodiments, the binding of IgM antibodies is detected through the use of an anti-human IgM antibody linked to a detectable moiety. In some embodiments, the detectable moiety is selected from the group consisting of chromophores, radioactive moieties, and enzymes. In some embodiments, the detectable moiety includes alkaline phosphatase. In certain embodiments, the detectable moiety includes biotin.

According to another aspect of the invention, a method for detecting IgG-class antibodies resulting from infection by a coronavirus, if present in a biological sample obtained from a subject suspected of having a coronavirus infection, is provided, the method including: a) providing a composition including at least four labelled and/or tagged and/or bound amino acid sequences, wherein the at least four labelled and/or tagged and/or bound amino acid sequences include amino acid sequences SEQ ID NO: 1, SEQ ID NO: 2, SEQ ID NO: 3, and SEQ ID NO: 4, and variants thereof which retain the immunological binding profile of the corresponding non-variant; b) providing the biological sample obtained from the subject suspected of having a coronavirus infection; c) contacting the biological sample with the composition of step a) under conditions appropriate for specific antibody binding to an epitope; and d) detecting specific binding of IgG-class antibodies with the amino acid sequences of step a), wherein the sample is scored as positive for coronavirus infection when positive binding is detected for: SEQ ID NO: 1 or SEQ ID NO: 3 and SEQ ID NO: 4; SEQ ID NO: 1 or SEQ ID NO: 3 and SEQ ID NO: 2; or SEQ ID NO: 2 and SEQ ID NO: 4. In some embodiments, the binding of IgG-class antibodies is detected through the use of an anti-human IgG antibody linked to a detectable moiety. In some embodiments, the amino acid sequences of step a) also include amino acid sequences SEQ ID NO: 5 and SEQ ID NO: 6 and variants thereof which retain the immunological binding profile of the corresponding non-variant; and wherein the sample is scored as positive for coronavirus infection when positive binding with IgG-class antibodies is detected for: SEQ ID NO: 1 or SEQ ID NO: 3 and SEQ ID NO: 2; SEQ ID NO: 1 or SEQ ID NO: 3 and SEQ ID NO: 4; SEQ ID NO: 1 or SEQ ID NO: 3 and SEQ ID NO: 5; SEQ ID NO: 1 or SEQ ID NO: 3 and SEQ ID NO: 6; SEQ ID NO: 2 and SEQ ID NO: 4; SEQ ID NO: 2 and SEQ ID NO: 5; SEQ ID NO: 2 and SEQ ID NO: 6; SEQ ID NO: 4 and SEQ ID NO: 5; SEQ ID NO: 4 and SEQ ID NO: 6; and SEQ ID NO: 5 and SEQ ID NO: 6. In certain embodiments, the binding of IgG-class antibodies is detected through the use of an anti-human IgG antibody linked to a detectable moiety. In some embodiments, the detectable moiety is selected from the group consisting of chromophores, radioactive moieties, and enzymes. In some embodiments, the detectable moiety includes alkaline phosphatase. In certain embodiments, the detectable moiety includes biotin.

According to another aspect of the invention, a method for detecting IgA-class antibodies resulting from infection by a coronavirus, if present in a biological sample obtained from a subject suspected of having a coronavirus infection, is provided, the method including: a) providing a composition including at least four labelled and/or tagged and/or bound amino acid sequences, wherein the at least four labelled and/or tagged and/or bound amino acid sequences include amino acid sequences SEQ ID NO: 1, SEQ ID NO: 2, SEQ ID NO: 3, and SEQ ID NO: 4, and variants thereof which retain the immunological binding profile of the corresponding non-variant; b) providing the biological sample obtained from the subject suspected of having a coronavirus infection; c) contacting the biological sample with the composition of step a) under conditions appropriate for specific antibody binding to an epitope; and d) detecting specific binding of IgA-class antibodies with the amino acid sequences of step a), wherein the sample is scored as positive for coronavirus infection when at least two of the amino acid sequences of step a) exhibit positive binding with IgA-class antibodies from the biological sample. In some embodiments, the binding of IgA-class antibodies is detected through the use of an anti-human IgA antibody linked to a detectable moiety. In some embodiments, the amino acid sequences of step a) also include amino acid sequences SEQ ID NO: 5 and SEQ ID NO: 6 and variants thereof which retain the immunological binding profile of the corresponding non-variant; and wherein the sample is scored as positive for coronavirus infection when at least two of the amino acid sequences of step a) exhibit positive binding with IgA-class antibodies from the biological sample. In certain embodiments, the binding of IgA-class antibodies is detected through the use of an anti-human IgA antibody linked to a detectable moiety. In some embodiments, the detectable moiety is selected from the group consisting of chromophores, radioactive moieties, and enzymes. In some embodiments, the detectable moiety includes alkaline phosphatase. In certain embodiments, the detectable moiety includes biotin.

According to another aspect of the invention, a vector including a nucleic acid sequence encoding an amino acid sequence selected from the group consisting of SEQ ID NO: 1, SEQ ID NO: 2, SEQ ID NO: 3, SEQ ID NO: 4, SEQ ID NO: 5, SEQ ID NO: 6, and variants thereof which retain the immunological binding profile of the corresponding non-variant is provided. In some embodiments, the nucleic acid molecule is operatively linked to a promoter sequence. In some embodiments, the vector is a prokaryotic vector. In certain embodiments, a cell including the vector is provided. In some embodiments, the cell is a bacterial cell.

Figure 1:
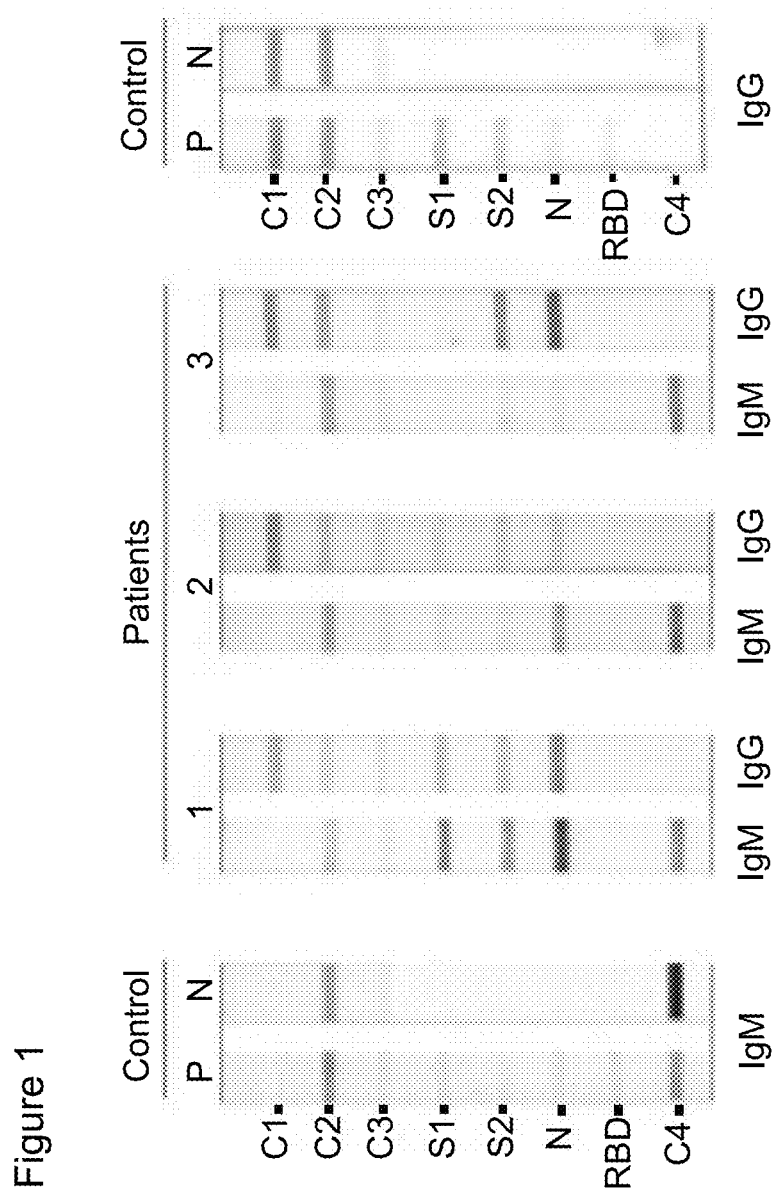
FIG. 1 provides a photomicrographic image of SARS-CoV-2 IgG and IgM immunoblots (IBs) with sera from three patients (1, 2, and 3) and positive (P) and negative (N) control human sera. The positive control (P) was pooled sera from patients positive for SARS-CoV-2 by real-time RT-PCR, and showed reactivity with S1, S2, N, and RBD polypeptides in both IgG and IgM IBs. The negative control (N) was pooled human sera from patients prior to August, 2019, and did not react with the four SARS-CoV-2 antigens. C1, purified IgG; C2, Protein L; C3, internal calibrator; C4, purified IgM. The positions of S1, S2, N, and RBD proteins in the membrane strips are also indicated.

DESCRIPTION OF THE SEQUENCES
SEQ ID NO: 1. Spike protein S1 domain
MRTQLPPAYTNSFTRGVYYPDKVFRSSVLHSTQDLFLPFFSNVTWFHAIHV

SGTNGTKRFDNPVLPFNDGVYFASTEKSNIIRGWIFGTTLDSKTQSLLIVN

-continued
NATNVVIKVCEFQFCNDPFLGVYYRKNNKSWMESEFRVYSSANNCTFEYVS

QPFLMDLEGKQGNFKNLREFVFKNIDGYFKIYSKHTPINLVRDLPQGFSAL

EPLVDLPIGINITRFQTLLALHRSYLTPGDSSSGWTAGAAAYYVGYLQPRT

FLLKYNENGTITDAVDCALDPLSETKCTLKSFTVEKGIYQTSNFRVQPTES

IVRFPNITNLCPFGEVFNATRFASVYAWNRKRISNCVADYSVLYNSASFST

FKCYGVSPTKLNDLCFTNVYADSFVIRGDEVRQIAPGQTGKIADYNYKLPD

DFTGCVIAWNSNNLDSKVGGNYNYLYRLFRKSNLKPFERDISTEIYQAGST

PCNGVEGFNCYFPLQSYGFQPTNGVGYQPYRVVVLSFELLHAPATVCGPKK

STNLVKNKCVNFNFNGLTGTGVLTESNKKFLPFQQFGRDIADTTDAVRDPQ

TLEILDITPCSFGGVSVITPGTNTSNQVAVLYQDVNCTEVPVAIHADQLTP

TWRVYSTGSNVFQTRAGCLIGAEHVNNSYECDIPIGAGICASYQTQTNSPR

RARSVASQSIIAYTMSLGAENSVAYSNNSIAIPTNFTISVTTEILPVSMTK

TSVDCTMYICGDSTECSNLLLQYGSFCTQLNRALTGIAVEQDKNTQEVFAQ

VKQIYKTPPIKDFGGFNFSQILPDPSKPSKRSFIEDLLFNKVTLADAGFIK

QYGDCLGDIAARDLICAQKFNGLTVLPPLLTDEMI.

SEQ ID NO: 2. S1 domain RBD region
MVQPTESIVRFPNITNLCPFGEVFNATRFASVYAWNRKRISNCVADYSVLY

NSASFSTFKCYGVSPTKLNDLCFTNVYADSFVIRGDEVRQIAPGQTGKIAD

YNYKLPDDFTGCVIAWNSNNLDSKVGGNYNYLYRLFRKSNLKPFERDISTE

IYQAGSTPCNGVEGFNCYFPLQSYGFQPTNGVGYQPYRVVVLSFELLHAPA

TVCGPKKSTNLVKNKCVN.

SEQ ID NO: 3. Spike protein S2 domain
MSLGAENSVAYSNNSIAIPTNFTIVFAQVKQIYKTPPIKDFGGFNFSQILP

DPSKPSKRSFIEDLLFNKVTLADAGFIKQYGDCLGDIAARDLICAQKFNGL

TVLPPLLTDEMIAQYTSALLAGTITSGWTFGAGAALQIPFAMQMAYRFNGI

GVTQNVLYENQKLIANQFNSAIGKIQDSLSSTASALGKLQDVVNQNAQALN

TLVKQLSSNFGAISSVLNDILSRLDKVEAEVQIDRLITGRLQSLQTYVTQQ

LIRAAEIRASANLAATKMSECVLGQSKRVDFCGKGYHLMSFPQSAPHGVVF

LHVTYVPAQEKNFTTAPAICHDGKAHFPREGVFVSNGTHWFVTQRNFYEPQ

IITTDNTFVSGNCDVVIGIVNNTVYDPLQPELDSFKEELDKYFKNHTSPDV

DLGDISGINASVVNIQKEIDRLNEVAKNLNESLIDL.

SEQ ID NO: 4. Nucleocapsid (N) phosphoprotein
MSDNGPQNQRNAPRITFGGPSDSTGSNQNGERSGARSKQRRPQGLPNNTAS

WFTALTQHGKEDLKFPRGQGVPINTNSSPDDQIGYYRRATRRIRGGDGKMK

DLSPRWYFYYLGTGPEAGLPYGANKDGIIWVATEGALNTPKDHIGTRNPAN

NAAIVLQLPQGTTLPKGFYAEGSRGGSQASSRSSSRSRNSSRNSTPGSSRG

TSPARMAGNGGDAALALLLLDRLNQLESKMSGKGQQQQGQTVTKKSAAEAS

KKPRQKRTATKAYNVTQAFGRRGPEQTQGNFGDQELIRQGTDYKHWPQIAQ

FAPSASAFFGMSRIGMEVTPSGTWLTYTGAIKLDDKDPNFKDQVILLNKHI

DAYKTFPPTEPKKDKKKKADETQALPQRQKKQQTVTLLPAADLDDFSKQLQ

QSMSSADSTQA.

SEQ ID NO: 5. NSP3 (ORF1A) papain-like protease
MEVRTIKVFTTVDNINLHTQVVDMSMTYGQQFGPTYLDGADVTKIKPHNSH

EGKTFYVLPNDDTLRVEAFEYYHTTDPSFLGRYMSALNHTKKWKYPQVNGL

TSIKWADNNCYLATALLTLQQIELKFNPPALQDAYYRARAGEAANFCALIL

AYCNKTVGELGDVRETMSYLFQHANLDSCKRVLNVVCKTCGQQQTTLKGVE

AVMYMGTLSYEQFKKGVQIPCTCGKQATKYLVQQESPFVMMSAPPAQYELK

HGTFTCASEYTGNYQCGHYKHITSKETLYCIDGALLTKSSEYKGPITDVFY

KENSYTTTIK.

SEQ ID NO: 6. ORF8 protein
MKFLVFLGIITTVAAFHQECSLQSCTQHQPYVVDDPCPIHFYSKWYIRVGA

RKSAPLIELCVDEAGSKSPIQYIDIGNYTVSCLPFTINCQEPKLGSLVVRC

SFYEDFLEYHDVRVVLDFI.

DETAILED DESCRIPTION OF THE INVENTION

COVID-19 is caused by a novel coronavirus, SARS-CoV-2. COVID-19 affects different subjects in different ways. Infected people have had a wide range of symptoms reported—from mild symptoms to severe illness as described above herein, and may also be asymptomatic while still being contagious. Because the symptoms of COVID-19 can mimic, for example, viral flu-like symptoms, accurate diagnosis of COVID-19 is important for identifying or confirming infected subjects, in order to provide effective treatment for the subject. In aspects, the present disclosure provides compositions and methods for a quick and easy diagnostic test for detecting the presence of coronavirus-specific antibodies, including SARS-CoV-2-specific antibodies, thereby satisfying the need for such a test.

Although a coronavirus only produces a specific set of viral proteins, immunological response profiles may vary among subjects. As used herein, the term "immunological response profile" refers to the set of coronavirus antigens to which a subject's immune system recognizes and binds. Infected subjects may have different immunological response profiles because they may not produce antibodies to the same viral proteins or viral protein fragments. Therefore, in order to capture diverse COVID-19 immunological response profiles and correctly identify a subject with a positive COVID-19 result, immunological tests for COVID-19 need to have high sensitivity and specificity, and need to be able to detect antibodies to more than one antigen. In aspects, the present disclosure solves this problem by providing multiple SARS-CoV-2-specific antigens to concurrently detect multiple SARS-CoV-2-specific antibodies among multiple antibody classes, including but not limited to IgM, IgG, and IgA.

Aspects of the present invention provide novel compositions and methods for diagnosing a coronavirus infection, including a SARS-CoV-2 infection. In aspects, the present disclosure provides compositions and methods for quickly and accurately detecting coronavirus-specific antibodies, in samples from subjects having positive NAAT coronavirus test results, suspected of having a coronavirus infection based on symptoms, or that may have been exposed to a coronavirus. In aspects, the present disclosure provides compositions and methods for quickly and accurately detecting SARS-CoV-2-specific antibodies in samples from subjects having positive NAAT COVID-19 results, suspected of having COVID-19 based on symptoms, or that may have been exposed to SARS-CoV-2.

The invention is based, in part, on the novel multiplexed use of coronavirus-specific amino acid sequences encoding antigenic peptides (which may also be referred to in the art and elsewhere herein as target antigens, target antigen polypeptides, peptide antigens, or antigens), as described herein.

In one aspect, a composition of the present disclosure comprises at least four labelled and/or tagged and/or bound amino acid sequences, wherein the at least four labelled and/or tagged and/or bound amino acid sequences comprise amino acid sequences SEQ ID NO: 1, SEQ ID NO: 2, SEQ ID NO: 3, and SEQ ID NO: 4, and variants thereof which retain the immunological binding profile of the corresponding non-variant. In embodiments, a composition of the present disclosure further comprises at least two labelled and/or tagged and/or bound amino acid sequences, wherein the at least two labelled and or tagged and/or bound amino acid sequences comprise amino acid sequences SEQ ID NO: 5 and SEQ ID NO: 6, and variants thereof which retain the immunological binding profile of the corresponding non-variant. In some embodiments, a composition of the disclosure comprises at least four labelled and/or tagged and/or bound amino acid sequences, wherein the at least four labelled and/or tagged and/or bound amino acid sequences have at least 75%, 80%, 85%, 90%, 95%, 98%, 99%, 99.5%, or 100% homology to SEQ ID NO: 1, SEQ ID NO: 2, SEQ ID NO: 3, SEQ ID NO: 4. In some embodiments, a composition of the disclosure comprises at least six labelled and/or tagged and/or bound amino acid sequences, wherein the at least six labelled and/or tagged and/or bound amino acid sequences have at least 75%, 80%, 85%, 90%, 95%, 98%, 99%, 99.5%, or 100% homology to SEQ ID NO: 1, SEQ ID NO: 2, SEQ ID NO: 3, SEQ ID NO: 4, SEQ ID NO: 5, and SEQ ID NO: 6. As used herein, a non-variant is an amino acid sequence with 100% sequence homology to SEQ ID NO: 1, SEQ ID NO: 2, SEQ ID NO: 3, SEQ ID NO: 4, SEQ ID NO: 5, or SEQ ID NO: 6. The term "immunological binding profile" as used herein refers to the ability of a labelled and/or tagged and/or bound amino acid sequence to be bound by antibodies present in a biological sample. Non-limiting examples of immunological binding profiles include FIGS. 1 and 2.

Sequences with less than 100% homology may be modified with one or more substitutions, deletions, insertions, or other modifications with respect to the amino acid sequences provided herein. Exemplary modifications include, but are not limited to conservative amino acid substitutions, which will produce molecules having functional characteristics similar to those of the molecule from which such modifications are made. Conservative amino acid substitutions are substitutions that do not result in a significant change in the activity or tertiary structure of a selected polypeptide or protein. Such substitutions typically involve replacing a selected amino acid residue with a different residue having similar physico-chemical properties. For example, substitution of Glu for Asp is considered a conservative substitution because both are similarly-sized negatively-charged amino acids. Groupings of amino acids by physico-chemical properties are known to those of skill in the art. The following groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). One of ordinary skill in the art can determine if sequences with less than 100% homology can bind naturally- or non-naturally-occurring SARS-CoV-2-related antibodies, as well as the sensitivity and specificity of the antibody to the modified sequences. One of ordinary skill in the art will be able to identify sequences with significant homology to SEQ ID NOs: 1-6 of the present invention that give acceptable or equivalent responses in the methods of the present invention without undue experimentation, in view of the teachings of this specification.

In some embodiments, the present invention is a composition comprising at least four labeled and/or tagged and/or bound amino acid sequences, wherein the one or more labeled and/or tagged and/or bound amino acid sequences comprise amino acid sequences selected from the group consisting of SEQ ID NO: 1, SEQ ID NO: 2, SEQ ID NO: 3, SEQ ID NO: 4, and variants thereof which retain the immunological binding profile of the corresponding non-variant. In some embodiments, the present invention is a composition comprising six labeled and/or tagged and/or bound amino acid sequences, wherein the one or more labeled and/or tagged and/or bound amino acid sequences comprise amino acid sequences selected from the group consisting of SEQ ID NO: 1, SEQ ID NO: 2, SEQ ID NO: 3, SEQ ID NO: 4, SEQ ID NO: 5 and SEQ ID NO: 6 and variants thereof which retain the immunological binding profile of the corresponding non-variant. As used herein, "consisting of", when used as a claim transition referring to an amino acid sequence, refers to amino acid sequences having 100% homology to the specified amino acid sequence (i.e., SEQ ID NOs: 1-6).

Aspects of the present invention provide antigen-specific amino acid sequences for SARS-CoV-2. These novel amino acid sequences may be used in assays to identify SARS-CoV-2-specific antibodies in samples from subjects having positive NAAT COVID-19 results, in samples from subjects suspected of having COVID-19 based on symptoms, or in samples from subjects that may have been exposed to SARS-CoV-2. With the amino acid sequences of the present invention, identification of SARS-CoV-2 in subject samples is performed with greater speed, sensitivity, and specificity than other current methods. The amino acid sequences of the present invention may be used in diagnostic and scientific assays. Non-limiting examples of suitable assays include immunoblots, line immunoblots, ELISA (enzyme-linked immunosorbent assay), etc. The amino acid sequences of the present invention may be used for the detection of SARS-CoV-2 specific T-cells, for example, with the IgXSPOT test (IGeneX, Milpitas, CA).

In some embodiments, the invention is a composition comprising at least four labeled and/or tagged and/or bound amino acid sequences, wherein the at least four labeled and/or tagged and/or bound amino acid sequences comprise amino acid sequences selected from the group consisting of SEQ ID NO: 1, SEQ ID NO: 2, SEQ ID NO: 3, SEQ ID NO: 4, SEQ ID NO: 5, and SEQ ID NO: 6, and variants of those sequences. The expression "variants" encompasses any modification(s) of a specified amino acid sequence (i.e., SEQ ID NOs: 1-6) which retain(s) the immunological binding profile of the corresponding non-variant. Such modifications may include insertions and deletions (internal or from the N- or C-terminus, or both).

Nucleic acid sequences, including polynucleotides and oligonucleotides, encoding the amino acid sequences of the present invention, and portions thereof, may be expressed in cultured cells to provide isolatable quantities of peptides displaying biological (e.g., immunological) properties of the antigenic peptide encoded by the amino acid sequences of the present invention. Because of redundancy of the genetic code, multiple nucleic acid sequences may be suitable for the production of the peptide sequences of the present invention. One of ordinary skill in the art will be able to determine one or more nucleic acid sequences for production of the amino acid sequences of the present invention. A nucleic acid sequence encoding an amino acid sequence of the present invention may be labeled by any suitable label known to one of ordinary skill in the art.

In this regard, nucleic acid sequences suitable for the production of the amino acid sequences of the present invention may be substantially homologous to naturally occurring sequences. Substantial homology of a nucleic acid sequence as used herein means that: (a) there is greater than 65%, 70%, 75%, 80%, 85%, 90%, 95%, 98%, or 99% homology with the naturally occurring sequence, or (b) the homologous nucleic acid sequence will hybridize to the compared sequence or its complementary strand under stringent conditions of the temperature and salt concentration. These stringent conditions will generally be a temperature greater than about 22° C., usually greater than about 30° C. and more usually greater than about 45° C., and a salt concentration generally less than about 1 M, usually less than about 500 mM, and preferably less than about 200 mM. The combination of temperature and salt concentration is more important in defining stringency than either the temperature or the salt concentration alone. Other conditions which affect stringency include GC content of the compared sequence, extent of complementarity of the sequences, and length of the sequences involved in the hybridization, as well as the composition of buffer solution(s) used in the hybridization mixture. These and other factors affecting stringency are well described in the scientific and patent literature. One of ordinary skill in the art will be able to determine suitable conditions for determining the homology of the nucleic acid sequences encoding the antigenic peptides of the present invention.

Homologous nucleic acid sequences may be determined based on the nature of a nucleotide substitution in the nucleic acid sequence. For example, synonymous nucleotide substitutions, that is, nucleotide changes within a nucleic acid sequence that do not alter the encoded amino acid sequence, will be better tolerated and, therefore, may be more numerous in a particular nucleic acid sequence than non-synonymous nucleotide substitutions. One of ordinary skill in the art will be able to determine the suitable number and location of substitutions that may be allowed in a nucleic acid sequence that encodes an amino acid sequence of the present invention without adversely affecting the antigenicity of the encoded antigenic peptide, without undue experimentation.

Viral Infection

A viral infection, which may also be referred to as a viral disease, results in a cell or subject when a pathogenic virus is present in a cell or subject, or contacts a cell or subject, and infectious virus particles (virions) attach to and enter one or more cells. A viral infection in a cell, as referenced herein, means a cell into which virions have entered. A virally infected cell may be in a subject (in vivo) or obtained from a subject. In some embodiments, a virally infected cell is a cell in culture (in vitro), or is an infected cell obtained from culture. Numerous viruses, including coronaviruses and SARS-CoV-2, are known to infect subjects and cells.

As used herein, the term "viral particle" refers to an infectious viral particle or virion, whose main function is to deliver its genome (DNA or RNA) into a host cell so that its genome can be expressed, e.g., transcribed and translated, by the host cell. A complete viral particle includes one or more types of viral proteins and at least one complete copy of the viral genome. Several main types of viral proteins exist, include structural proteins, non-structural proteins, and regulatory and accessory proteins. Viral structural proteins include capsid proteins, envelope proteins, and membrane fusion proteins; viral non-structural proteins include proteins involved in replicon (replication complex) formation and immunomodulation (modulating the immune response of a subject to an infected cell). Viral regulatory and accessory proteins have a variety of functions, including but not limited to controlling viral gene expression in the host cell. The number and function(s) of each type of viral protein vary from virus to virus. In some embodiments, a viral protein is a spike (S) protein, a nucleocapsid (N) protein, an NSP3 protein, or an ORF8 protein. In embodiments, a viral protein may have multiple antigenic domains.

Symptoms

A viral infection in a subject may be symptomatic or asymptomatic. A symptomatic viral infection may result in clinical symptoms in a subject infected with the virus including, but not limited to fever, shortness of breath, difficulty breathing, loss of sense of taste and/or smell, low blood oxygenation saturation, chills, vomiting, diarrhea, headache, muscle aches/pain, weakness, loss of appetite, malaise, nasal congestion, body aches, cough, sore throat, runny nose, and sneezing. Severity of a viral infection varies with different viruses and in different subjects. For example, a first subject with a viral infection may exhibit one or more symptoms such as, fever, chills, cough, etc. and a second subject with a more severe infection with the virus may exhibit some or all of the symptoms of the first subject, and also one or more of symptoms such as but not limited to trouble breathing, confusion, inability to stay awake, bluish lips or face, pain or pressure in chest, and significantly low blood oxygen saturation. It will be understood that clinical symptoms in a subject with a viral infection can be assessed and the symptoms identified by a health-care professional.

Labels and Tags

One or more amino acid sequences of the invention may be labeled and/or tagged and/or bound. As used herein, a "label" or "tag" is a detectable moiety that may be attached to an amino acid sequence of the invention. A label or tag may be covalently or non-covalently attached to an amino acid sequence of the invention. Non-limiting examples of such "tags" are natural and synthetic (i.e., non-naturally occurring) nucleic acid and amino acid sequences (e.g., poly-AAA tags), antibodies and detectable moieties such as labels (discussed elsewhere herein). Thus, the definitions of the phrases "labeled" and "tagged" may have overlap in that a tag may also, in some instances, function as a label. Furthermore, tags useful with the present invention may be linked to a label.

The amino acid sequences of the present invention, or any tags attached to an amino acid sequence of the present invention, may be labeled with any suitable label known to one of ordinary skill in the art. Such labels may include, but are not limited to, biotin/streptavidin, enzyme conjugates (e.g., horseradish peroxidase (HRP), alkaline phosphatase (AP), glucose oxidase, and β-galactosidase), fluorescent moieties (e.g., FITC, fluorescein, rhodamine, etc.), biological fluorophores (e.g., green fluorescent protein (GFP), R-phycoerythrin) or other luminescent proteins, etc. Any suitable label known to one of ordinary skill in the art may be used with the present invention.

In some embodiments, amino acid sequences of the invention may be "bound." A "bound" amino acid sequence is an amino acid sequence that has been immobilized in order to permit the use of the amino acid sequence in a biological test such as, for example, an immunoassay. In the context of the present invention, a "bound" amino acid sequence is an amino acid sequence attached (e.g., covalently or non-covalently bound, etc.) directly or indirectly to a non-natural surface or substance, e.g, a solid support. Additionally or alternatively, "bound" amino acid sequences of the present invention may be attached, directly or indirectly, to a natural surface or substance, e.g, a solid support, either of which is not naturally associated with the amino acid sequence. Non-limiting examples of substances to which the amino acid sequences of the present invention may be bound are nitrocellulose, nylon, polyvinylidene difluoride (PVDF) plastics, metals, magnetic beads and agarose (e.g., beads). Linking agents known to those of ordinary skill in the art may be used to aid or enhance binding of the amino acid sequences of the present invention to a surface or sub stance.

Production of Amino Acid Sequences

In some embodiments, amino acid sequences of the invention may be non-natural, synthetic sequences, such as sequences produced by recombinant technology or sequences synthesized by protein synthesizing apparatuses. As such, the amino acid sequences of the present invention may be produced by recombinant technology, as is described and enabled in the literature and in commonly referred to manuals such as, e.g., Short Protocols in Molecular Biology, Second Edition, F. M. Ausubel, Ed., all John Wiley & Sons, N.Y., edition as of 2008; and, Sambrook, et al., Molecular Cloning: A Laboratory Manual, 3rd ed., Cold Spring Harbor Laboratory Press, Cold Spring Harbor, 2001, and as is well known to one of ordinary skill in the art. In one embodiment, the amino acid sequences of the present invention are made recombinantly in *E. coli*, or another prokaryotic bacterium.

As used herein, the term "vector" refers to a nucleic acid molecule capable of transporting between different genetic environments another nucleic acid to which it has been operatively linked. In addition to the nucleic acid sequence encoding an amino acid sequence selected from the group consisting of SEQ ID NO: 1, SEQ ID NO: 2, SEQ ID NO: 3, SEQ ID NO: 4, SEQ ID NO: 5, and SEQ ID NO: 6 and variants thereof which retain the immunological binding profile of the corresponding non-variant, the vectors of the present invention also include a heterologous nucleic acid sequence. As used herein, heterologous refers to a nucleic acid sequence that does not naturally occur in a coronavirus, including but not limited to SARS-CoV-2. The term "vector" may also refer to a virus or organism that is capable of transporting the nucleic acid molecule. One type of vector is a plasmid, a small, circular, double-stranded, extrachromosomal DNA molecule that is physically separate from and can self-replicate independently from chromosomal DNA. Some useful vectors are those capable of autonomous replication and/or expression of nucleic acids to which they are linked. Vectors capable of directing the expression of nucleic acids to which they are operatively linked are referred to herein as "expression vectors." Other useful vectors, include, but are not limited to bacterial plasmids and bacterial artificial chromosomes (BACs), cosmids, and viruses such as lentiviruses, retroviruses, adenoviruses, and phages. Prokaryotic vectors are commonly used for the production of recombinant peptides. Cells are transformed with the vectors encoding a recombinant amino acid sequence of interest, and the cells are grown. Following growth to an appropriate density, cells are lysed and recombinant peptides are isolated through conventional techniques.

Vectors useful in methods of the invention may include additional sequences including, but not limited to, one or more signal sequences and/or promoter sequences, or a combination thereof. Promoters that may be used in methods and vectors of the invention include, but are not limited to, cell-specific promoters or general promoters. Non-limiting examples of promoters that can be used in vectors of the invention are: ubiquitous promoters, such as, but not limited to: CMV, CAG, CBA, and EF1a promoters. Methods to select and use suitable promoters are well known in the art.

Vectors useful in methods of the invention may be used to express a fusion protein comprising sequences of the invention in a cell. Expression vectors and methods of their preparation and use are well known in the art. In some embodiments of the invention, a nucleic acid sequence of an expression vector encodes a fusion protein comprising an amino acid sequence of the invention. It is well known in the art how to prepare and utilize fusion proteins that comprise a polypeptide sequence. In some embodiments, a fusion protein comprising an amino acid sequence of the invention may also include an epitope tag that may be used for purification of the fusion protein or in a method of the invention. Non-limiting examples of epitope tags are a FLAG tag, a fluorescent tag (including but not limited to green fluorescent protein (GFP)), a GST tag, a hemagglutinin (HA), a poly-histidine (poly-His) tag, a Myc tag, an MBP tag, or a V5 tag. In some embodiments, a fusion protein comprising an amino acid sequence of the invention may also include a detectable label, as described elsewhere herein.

Assays and Methods of Detection

Specificity for an amino acid sequence, i.e., antibody specificity, is the property of antibodies which enables them to react preferentially with some antigenic determinants and not with others. Specificity is dependent on chemical composition, physical forces and molecular structure at the binding site. Sensitivity is how strongly the antibody binds to the antigenic determinant. One of ordinary skill in the art can determine specificity and sensitivity of an antibody for a particular amino acid sequence using standard affinity assays, such as immunoblotting, Ouchterlony assays, titer assays, etc. In another aspect, the present invention provides a method of quickly and accurately detecting SARS-CoV-2 antisera in a sample from a subject suspected of having COVID-19. The method of the present invention for detecting SARS-CoV-2 antisera in a sample from a subject suspected of having COVID-19, may comprise, for example, providing a biological sample (including but not limited to blood, saliva, nasal, throat swab) obtained from a subject suspected of having COVID-19, mixing the biological sample with one or more of the labeled and/or tagged and/or bound amino acid sequences of the present invention and detecting a positive reaction which indicates the presence of SARS-CoV-2 antisera in the sample. The antisera may be detected by, for example, immunoblotting, line immunoblotting, ELISPOT, ELISA, Western blotting, or any other appropriate immunoassay known to one of ordinary skill in the art. These techniques are known to one of ordinary skill in the art and procedures can be found in common technical references. While similar, each of these techniques has its advantages and disadvantages. Other suitable techniques may be known to those of skill in the art and are incorporated herein.

With a procedure called immunoblotting, known proteins can be bound to the solid medium and samples, such as samples from subjects suspected of having an infection, can be tested for the presence of specific antibodies in the sample by contacting the bound protein with the sample. An antibody that binds the target protein is usually referred to as the primary antibody. A secondary antibody, specific for conserved regions of the primary antibody (for example, a rabbit-anti-human IgG antibody may be used to detect primary human antibodies) is used to detect any bound primary antibodies. The secondary antibody is usually labeled with a detectable moiety for visualization. Non-limiting examples of suitable labels include, for example, chromophores such as biotin, radioactive moieties and enzymes such as alkaline phosphatase, etc. The use of these and other materials for the visualization of antibodies are well known to one of ordinary skill in the art. Immunoblotting offers sensitivity and specificity advantages as compared to, for example, ELISA assays, because in immunoblots, individual antigens are spotted at different positions on the blot whereas in ELISA, antigens are mixed. Thus the signal in ELISA is equivalent to signal due to all the antigens combined, whereas in Immunoblot, individual antigen bands are read. To assess the impact of testing limitations and to determine levels of exposure to SARS-CoV-2, a modified Western blot procedure, the line immunoblot, was employed in aspects of the invention described herein. Line immunoblots may be advantages for rapid, multiplex testing because of their small size and strip configuration. As used herein, line immunoblots used recombinant antigens from SARS-CoV-2 for diagnosis of COVID-19 in serum from patients and serological identification.

Western blotting can involve separating proteins by electrophoresis and then transferring to nitrocellulose or other solid media (e.g., polyvinylidene fluoride or PVDF-membrane and nylon membrane), and is described in more detail below. Immunoblotting can also involve applying proteins to a solid media manually or by machine. Preferably, the proteins are applied in straight lines or spots and dried, binding them to the solid support medium, e.g., nitrocellulose. The proteins used in an immunoblot can be isolated from biological samples or produced by recombinant technology, as is well known by those of ordinary skill in the art. The bound proteins are then exposed to a sample or samples suspected of having antibodies specific for the target proteins. With this procedure, a known antibody can be used to determine if a protein is present in a sample, such as when the proteins of lysed cells are separated by electrophoresis and transferred to the solid medium. Western blotting allows for the identification of proteins by size as well as by specificity for a specific antibody.

The Enzyme-Linked ImmunoSpot (ELISPOT) method can detect human T-cells that respond to SARS-CoV-2 specific antigens in vitro. In an ELISPOT assay, the surfaces of PVDF membrane in a 96-well microtiter plate are coated with capture antibody that binds, for example, anti-Interferon gamma (IFNγ) or other cytokine-specific antibody. During the cell incubation and stimulation step, the T-cells isolated from patient whole blood are seeded into the wells of the plate along with aforementioned sequence(s), and form substantially a monolayer on the membrane surface of the well. Upon stimulation of any antigen-specific cells with one or more of the sequences of the present invention they are activated and they release the IFNγ, which is captured directly on the membrane surface by the immobilized antibody. The IFNγ is thus "captured" in the area directly surrounding the secreting cell, before it has a chance to diffuse into the culture media, or to be degraded by proteases and bound by receptors on bystander cells. Subsequent detection steps visualize the immobilized IFNγ as an ImmunoSpot; essentially the secretory footprint of the activated cell.

For a specific example of an ELISPOT test, each well of the plate is coated with a purified cytokine-specific antibody specific for the test or cell being detected. T-cells are isolated from a subject (for example, a subject suspected of having COVID-19 infection or has been recently vaccinated) and cultured in each well and stimulated with recombinant antigens of one or more sequences of the present invention. COVID-19-positive patient cells secrete cytokine in response to stimuli, which is captured by the antibody coated in the well and further detected by ELISA.

ELISA assays may also be used to detect antigens. ELISA assays permit quantification of a specific protein in a mix of proteins (for example, a lysate) or may be used to determine if a peptide is present in a sample. Likewise, ELISA assays may be used to determine if a specific antibody is present by using a specific antigen as a target. As used with the present invention, target amino acid sequence(s) are attached to a surface. Then, if present in the sample being tested, the reactive antibody can bind to the antigen. A secondary antibody linked to an enzyme is added, and, in the final step, a substance containing the enzyme's substrate is added. The subsequent reaction produces a detectable signal, most commonly a color change in the substrate.

In one aspect of a method of the present invention, a biological sample obtained from a subject suspected of having a coronavirus infection is scored as positive for coronavirus infection when the biological sample is contacted with at least four labelled and/or tagged and/or bound amino acid sequences comprising amino acid sequences SEQ ID NO: 1, SEQ ID NO: 2, SEQ ID NO: 3, and SEQ ID NO: 4, and variants thereof which retain the immunological binding profile of the corresponding non-variant, under conditions appropriate for specific antibody binding to an epitope, and at least two of the at least four labelled and/or tagged and/or bound amino acid sequences exhibit positive binding with IgM-class antibodies from the biological sample. In some embodiments, a positive result is indicated when the biological sample is contacted with six labelled and/or tagged and/or bound amino acid sequences comprising amino acid sequences SEQ ID NO: 1, SEQ ID NO: 2, SEQ ID NO: 3, and SEQ ID NO: 4, SEQ ID NO: 5, and SEQ ID NO: 6, and variants thereof which retain the immunological binding profile of the corresponding non-variant, under conditions appropriate for specific antibody binding to an epitope, and at least two of the six labelled and/or tagged and/or bound amino acid sequences exhibit positive binding with IgM-class antibodies from the biological sample.

In one aspect of a method of the present invention, a biological sample obtained from a subject suspected of having a coronavirus infection is scored as positive for coronavirus infection when the biological sample is contacted with at least four labelled and/or tagged and/or bound amino acid sequences comprising amino acid sequences SEQ ID NO: 1, SEQ ID NO: 2, SEQ ID NO: 3, and SEQ ID NO: 4, and variants thereof which retain the immunological binding profile of the corresponding non-variant, under conditions appropriate for specific antibody binding to an epitope, and positive binding by IgG-class antibodies is detected for SEQ ID NO: 1 or SEQ ID NO: 3 and SEQ ID NO: 4; SEQ ID NO: 1 or SEQ ID NO: 3 and SEQ ID NO: 2; or SEQ ID NO: 2 and SEQ ID NO: 4. In some embodiments, a biological sample obtained from a subject suspected of having a coronavirus infection is scored as positive for coronavirus infection when the biological sample is contacted with six labelled and/or tagged and/or bound amino acid sequences comprising amino acid sequences SEQ ID NO: 1, SEQ ID NO: 2, SEQ ID NO: 3, and SEQ ID NO: 4, SEQ ID NO: 5, and SEQ ID NO: 6, and variants thereof which retain the immunological binding profile of the corresponding non-variant, under conditions appropriate for specific antibody binding to an epitope, and positive binding by IgG-class antibodies is detected for SEQ ID NO: 1 or SEQ ID NO: 3 and SEQ ID NO: 2; SEQ ID NO: 1 or SEQ ID NO: 3 and SEQ ID NO: 4; SEQ ID NO: 1 or SEQ ID NO: 3 and SEQ ID NO: 5; SEQ ID NO: 1 or SEQ ID NO: 3 and SEQ ID NO: 6; SEQ ID NO: 2 and SEQ ID NO: 4; SEQ ID NO: 2 and SEQ ID NO: 5; SEQ ID NO: 2 and SEQ ID NO: 6; SEQ ID NO: 4 and SEQ ID NO: 5; SEQ ID NO: 4 and SEQ ID NO: 6; and SEQ ID NO: 5 and SEQ ID NO: 6.

In one aspect of a method of the present invention, a biological sample obtained from a subject suspected of having a coronavirus infection is scored as positive for coronavirus infection when the biological sample is contacted with at least four labelled and/or tagged and/or bound amino acid sequences comprising amino acid sequences SEQ ID NO: 1, SEQ ID NO: 2, SEQ ID NO: 3, and SEQ ID NO: 4, and variants thereof which retain the immunological binding profile of the corresponding non-variant, under conditions appropriate for specific antibody binding to an epitope, and at least two of the at least four labelled and/or tagged and/or bound amino acid sequences exhibit positive binding with IgA-class antibodies from the biological sample. In some embodiments, a positive result is indicated when the biological sample is contacted with six labelled and/or tagged and/or bound amino acid sequences comprising amino acid sequences SEQ ID NO: 1, SEQ ID NO: 2, SEQ ID NO: 3, SEQ ID NO: 4, SEQ ID NO: 5, and SEQ ID NO: 6, and variants thereof which retain the immunological binding profile of the corresponding non-variant, under conditions appropriate for specific antibody binding to an epitope, and at least two of the six labelled and/or tagged and/or bound amino acid sequences exhibit positive binding with IgA-class antibodies from the biological sample.

In methods of the present invention, any primary antibody bound to a peptide encoded by an amino acid sequence of the present invention may be detected with anti-human antibodies, such as IgG, IgM, or IgA, used as the secondary antibody conjugated to a detectable moiety. As described elsewhere herein, the detectable moiety may be selected from the group consisting of chromophores, radioactivity moieties and enzymes or other detectable moiety known to one of ordinary skill in the art. In one embodiment, the detectable moiety comprises alkaline phosphatase. In another embodiment the detectable moiety comprises biotin.

In some embodiments of the invention, a sample may be considered positive in an assay for SARS-CoV-2 if at least two amino acid sequences are detected. In some embodiments of the invention, a sample may be considered positive for a specific strain of SARS-CoV-2 if at least two amino acid sequences identified with that specific strain are detected.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated by reference in their entirety herein.

EXAMPLES

Example 1. Sensitivity and Specificity of SARS-CoV-2 IgM and IgG ImmunoBlots

SARS-CoV-2 IgG and IgM ImmunoBlot (IB) tests, qualitative immunoblot assays, were designed and performed to detect IgG and IgM antibodies directed against SARS-CoV-2 in serum samples of patients confirmed to have COVID-19 by SARS-CoV-2 real-time RT-PCR. Recombinant SARS-CoV-2 antigens were sprayed as straight lines onto nitrocellulose strips, which were then used in the SARS-CoV-2 ImmunoBlot Test. Experiments were undertaken to determine the sensitivity and specificity of the SARSCOV-2 ImmunoBlot Test.

Methods

Antigen Preparation

Four recombinant target polypeptides of SARS-CoV-2, S1, S2, RBD, and N were obtained by cloning hybrid gene constructs or portions of genes into pET vectors and expressing the gene products in *Escherichia coli* (GenScript, Piscataway, NJ). The recombinant proteins were then isolated and extensively purified as previously described [Liu S. et al., *Healthcare* 6, 99 (2018); Shah J. S. et al., *Healthcare*

7(4), 121 (2019)]. The N protein (GenBank accession QHD43423.2, amino acid residues 1-419; SEQ ID NO: 4), the spike protein (GenBank accession QHD43416.1) S1 domain composed of amino acid residues 16-690 (SEQ ID NO: 1), the spike protein S2 domain (amino acid residues 698-1213; SEQ ID NO: 3), and the RBD region of the S1 (amino acid residues 319-541; SEQ ID NO: 2) were used as target antigens in the IBs. Protein BLAST analysis showed that the N and S target antigens used in the IBs had ≥99.76% and ≥98.84% sequence homologies, respectively, to the corresponding protein sequences from other SARS-CoV-2 isolates (taxid 694009) deposited in the GenBank database. The N and S SARS-CoV-2 proteins used in IBs had lower sequence homologies of ≤34% and ≤33% to the respective N and S proteins from four human coronaviruses (HCoVs OC43, HKU1, 229E, and NL63) that cause common cold symptoms.

Preparation of Antigen Strips

Antigen strips for SARS-CoV-2 immunoblots were prepared as previously described [Liu S. et al., *Healthcare* 6, 99 (2018); Shah J. S. et al., *Healthcare* 7(4), 121 (2019)]. Purified target antigen polypeptides and control proteins were diluted to yield approximately 12 ng of protein per line (with a range of 7-19 ng protein/line) and were sprayed in straight lines onto nitrocellulose membrane sheets (Cytiva, Marlborough, MA) using a BioDot liquid dispenser (BioDot, Irvine, CA). Human IgG and IgM (Sigma, St. Louis, MO, USA) were applied as controls C1 and C4, respectively, on all IB strips for establishing the specificity of antibody class detection and for confirming the addition of alkaline phosphatase-conjugated anti-human antibodies. Control C2, Protein L (Sigma, St. Louis, MO, USA) was used for detecting the addition of human serum as previously described [Liu S. et al., *Healthcare* 6, 99 (2018); Shah J. S. et al., *Healthcare* 7(4), 121 (2019)]. A calibrator standard C3 was applied on the test strip for use in all IB assays. The sheets were then blocked with 5% dried non-fat milk and sliced into 3 mm wide strips. The prepared strips could be stored at ambient temperature for at least six months before their use in IB assays.

Immunoblotting

IgG and IgM antibodies to the target antigens were detected in the SARS-CoV-2 IBs as previously described [Liu S. et al., *Healthcare* 6, 99 (2018); Shah J. S. et al., *Healthcare* 7(4), 121 (2019)]. Prior to use, each strip was labeled and then soaked in 1 ml of diluent (100 mM Tris, 0.9% NaCl, 0.1% Tween-20 and 1% dried non-fat milk) for 5 min in a trough. A 10 µL aliquot of the test or control serum for IgG and 20 µL for IgM, was then added to the IB strip. The strips were next incubated at ambient temperature for one hour with serum, followed by three washes with wash buffer (KPL, Gaithersburg, MD, USA). After aspirating the final wash solution, strips for detecting IgG and IgM were incubated with alkaline phosphatase-conjugated goat anti-human IgG at 1:10,000 dilution and goat anti-human IgM at 1:3000 dilution respectively (KPL, Gaithersburg, MD, USA) for one hour at ambient temperature. After three washes, bands were visualized by reaction with 5-bromo-4-chloro-3-indolylphosphatenitro-blue tetrazolium (BCIP/NBT, KPL, Gaithersburg, MD, USA). The reactions were terminated by washing with distilled water when the calibration standard C3 produced a visible band. Antigen-reactive bands of lower intensity than the calibration standard were considered negative. The specificities of the goat anti-human IgG and goat anti-human IgM antisera were confirmed by their specific reactions only with human IgG (C1) and IgM (C4) controls, respectively, on the IB strips.

Scoring of Immunoblots

Recognition of a combination of two target antigen polypeptides, S1 or S2 and N, S1 or S2 and RBD, and N and RBD, was scored as an overall positive reaction for IgG antibodies. Reaction with any two of the target antigens, S1, S2, RBD, and N, was scored as an overall positive reaction for IgM antibodies.

Results

Clinical Specificity

A total of 231 human sera collected prior to August, 2019 and expected to be negative for SARS-CoV-2 ("pre-pandemic sera"), were obtained from the College of American Pathologists, New York State Department of Health, New York Biologics (Southampton, NY, USA), National Institutes of Health (Bethesda, MD), BEI Resources (Manassas, VA) and IGeneX (Table 1). The IGeneX samples were leftover sera that would otherwise have been discarded that were received for routine testing for tick-borne diseases. Thirty two goat antisera against different human influenza A and B strain viral proteins (hemagglutinin, neuraminidase, matrix protein and ribonucleoprotein) from BEI Resources were used as additional specificity controls.

TABLE 1

Reference human sera for determining specificity of the SARS-CoV-2 immunoblots

| Source | Characteristic | Number of sera |
|---|---|---|
| IGeneX (human sera) | Pre-pandemic sera received for tick-borne diseases testing | 152 |
| CAP and NYSHD Autoimmunity and Allergy (human sera) | Anti-nuclear antibody positive | 5 |
| | Anti-dsDNA antibody positive | 2 |
| | Rheumatoid factor positive | 12 |
| | Rheumatoid factor negative | 7 |
| | Elevated IgG | 13 |
| | Elevated IgE | 4 |
| | Normal IgE | 2 |
| NYB Viral Infections (human sera) | Epstein-Barr virus infection | 7 |
| | Herpes Simplex virus infection | 4 |
| | Cytomegalovirus infection | 4 |
| | Hepatitis C infection | 5 |
| | HIV infection | 7 |
| NIH, Bethesda, MD, AIDS Reagent Program (human sera) | HIV infection | 3 |
| BEI Resources, Manassas, VA (human sera) | Respiratory syncytial virus infection | 4 |
| BEI Resources, Manassas, VA (goat antisera) | Goat antisera to human influenza A virus proteins | 27 |
| | Goat antisera to human influenza B virus proteins | 5 |

CAP: College of American Pathologists; NYB: New York Biologics, Southampton, NY, USA; NYSH: New York State Department of Health; NIH: National Institutes of Health; BEI: Biodefense and Emerging Infections Research Resources Repository; ds: double-stranded.

Using the reading criteria described above, two IGeneX control pre-pandemic sera showed positive reactions in the SARS-CoV-2 IgG IBs and a different serum reacted positively in the SARS-CoV-2 IgM IB. The other positive reactions arose from two sera from patients with autoimmune conditions. A serum with elevated IgG gave a positive reaction in the SARS-CoV-2 IgG IB and another with rheumatoid factor reacted positively in the SARS-CoV-2 IgM IB. The findings with the 263 reference sera therefore yielded estimated analytical specificities of 98.9% (95% confidence interval or CI of 96.4%-99.7%) and 99.2% (95% CI of 97.0%-99.9%) for detecting IgG and IgM antibodies in the SARS-CoV-2 IgG IBs and SARS-CoV-2 IgM IBs, respectively.

Clinical Sensitivity

Eighty four serum samples were tested for both IgG and IgM antibodies in the SARS-CoV-2 IBs. The sera originated from 37 patients in different states in the USA and were sent for antibody testing at IGeneX by physicians following a positive real-time RT-PCR result for SARS-CoV-2 in the FDA EUA-authorized Quest Diagnostics RC SARS-CoV-2 or LabCorp COVID-19 real-time RT-PCR tests. The 37 patients had shown mild symptoms of SARS-CoV-2 infection and none had required hospitalization. No further clinical details were available for the 37 patients. All 37 patients provided serum samples at times that ranged from 0 to 154 days after the positive real-time RT-PCR test. The patients were 19 males and 18 females with an age range of 21 to 76 years.

Detection of Antibodies in Sera of Patients with SARS-CoV-2 Infections by SARS-CoV-2 IB Assay Representative IBs with sera from three SARS-CoV-2 real-time RT-PCR positive patients and control sera are shown in FIG. 1. The three patient sera shown gave positive reactions for both IgG and IgM antibodies against S1, S2, and N. They demonstrate that SARS-CoV-2 IgG and IgM IBs provide a visually interpretable method for detecting antibodies in SARS-CoV-2 infections with results being obtained in less than three hours using pre-prepared antigen strips. The IBs also demonstrate that, because there is no cross-recognition of IgG and IgM with the two goat antisera to IgG and IgM used in the IB assays, the IgG IBs only detect IgG antibodies and the IgM IBs only IgM antibodies.

All but one of the 37 patients developed antibodies that were detected in either the SARS-CoV-2 IgG or IgM IBs, indicating an overall sensitivity of 97% for detecting an antibody response in the patients. Twenty-six patients were positive for IgM antibodies and 34 were positive for IgG antibodies, corresponding to sensitivity of 70.3% for IgM and 91.9% for IgG.

Discussion

The SARS-CoV-2 IB assay offers many advantages and the present data suggest that it approaches the optimal clinical sensitivity and specificity recommendations in the USA and UK for near-patient care serological tests for SARS-CoV-2. The IB test strips are stable to storage for at least 6 months. A result from pre-prepared IB membrane strips can be obtained in less than three hours after a serum or plasma becomes available, with minimal washing and reagent addition steps in the assay. Also, the assay provides a clear visible reading signal that is readily interpreted relative to an internal calibrator, and the signal is stable for several weeks. Furthermore, the IB assay can be readily adapted for detecting antibodies of other immunoglobulin classes, and in other relevant fluids e.g. saliva and tears, which is important because the mucosal IgA and blood IgG and IgM antibody responses differ significantly in SARS-CoV-2 infection. The IB assays can also be easily expanded to include additional viral antigens. Antibody titers for the two antibody classes can also be generated by using different dilutions of sera in the IB assays.

The criteria for antibody positivity utilized the necessary recognition of at least two different proteins for optimizing the specificity of both IgG and IgM SARS-CoV-2 IB assays. The RBD lies within the S1 region of the S protein but the detection of RBD by antibodies does not parallel the detection of S1, with RBD being detected by fewer sera and variably at different time periods compared with S1. Epitopes in regions other than the RBD in S1 are therefore importantly antigenic in patients. Antibodies to the RBD in particular and the more N terminal region of S1 are important for neutralizing virus infectivity by preventing binding to host cells. Some antibodies to S2 may also neutralize infectivity by inhibiting cell fusion and virus entry. Measurement of antibody titers in the IB assay may be important as IgG antibody titers to the S protein measured by ELISA correlate with virus-neutralizing antibody titers in persons vaccinated with S, although this correlation is weaker in non-hospitalized patients. Other data suggest that antibody levels to RBD and other viral antigens are higher in more severely ill hospitalized patients, which may be consistent with the poor anti-RBD antibody responses observed in the present study with sera from non-hospitalized patients.

These results also show the importance of detecting both IgG and IgM antibodies rather than either antibody class alone to better assess seroconversion after infection with SARS-CoV-2, which is consistent with findings in symptomatic patients from China. Furthermore, the results suggest that testing sera from individual patients obtained at different times after a positive real-time RT-PCR test, as well as early sera for IgM antibodies, may be important.

In conclusion, the SARS-CoV-2 IBs described herein provide a useful supplement to existing serological tests for confirming active or past infection, assessing antibody responses in patients with active disease, and sero-epidemiological studies on SARS-CoV-2 and COVID-19.

Example 2. Testing of Additional Target Antigens

Additional SARS-CoV-2 IgG and IgM ImmunoBlot (IB) tests, qualitative immunoblot assays, were designed and performed to detect IgG and IgM antibodies directed against SARS-CoV-2 in serum samples of patients confirmed to have COVID-19 by SARS-CoV-2 real-time RT-PCR. Recombinant SARS-CoV-2 antigens were sprayed as straight lines onto nitrocellulose strips, which were then used in the SARS-CoV-2 ImmunoBlot Test. Experiments were undertaken to determine the sensitivity and specificity of the SARSCOV-2 ImmunoBlot Test.

Methods

Antigen Preparation

S1, S2, RBD, and N recombinant target polypeptides were obtained and purified as described in Example 1 herein. Two additional SARS-CoV-2 target polypeptides NSP3 (SEQ ID NO: 5), and ORF8 (SEQ ID NO: 6) were obtained by cloning hybrid gene constructs or portions of genes into pET vectors, expressing the gene products in *Escherichia coli* (GenScript, Piscataway, NJ), then isolating the proteins to >90% purity, as previously described [Liu S. et al., *Healthcare* 6, 99 (2018); Shah J. S. et al., *Healthcare* 7(4), 121 (2019)]. Protein BLAST analysis showed that the NSP3 and ORF8 proteins used in the IBs had 100% sequence homologies, respectively, to the corresponding protein sequences from other SARS-CoV-2 isolates deposited in the GenBank database. The NSP3 SARS-CoV-2 protein used in IBs had lower sequence homologies of <30% to the respective protein from four human coronaviruses (HCoVs 0C43, HKU1, 229E, and NL63) that cause common cold symptoms. The ORF8 protein sequence had no significant sequence homologies to the respective protein from four human coronaviruses (HCoVs 0C43, HKU1, 229E, and NL63).

Preparation of Antigen Strips

Antigen strips for SARS-CoV-2 immunoblots were prepared as described in Example 1 herein. In some IBs, a mixture of purified IgM and IgG was used for the C1 control.

Immunoblotting

IgG and IgM antibodies were detected in the SARS-CoV-2 IBs as described in Example 1 herein.

Scoring of Immunoblots

Recognition of a combination of two proteins—S1 or S2 and RBD, S1 or S2 and N, S1 or S2 and NSP3, S1 or S2 and ORF8, RBD and N, RBD and NSP3, RBD and ORF8, N and NSP3, N and ORF8, and NSP3 and ORF8—was scored as an overall positive reaction for IgG antibodies and reaction with any two of the proteins—S1, S2, RBD, N, NSP3, and ORF8—as an overall positive reaction for IgM antibodies.

Results

Figure 2:
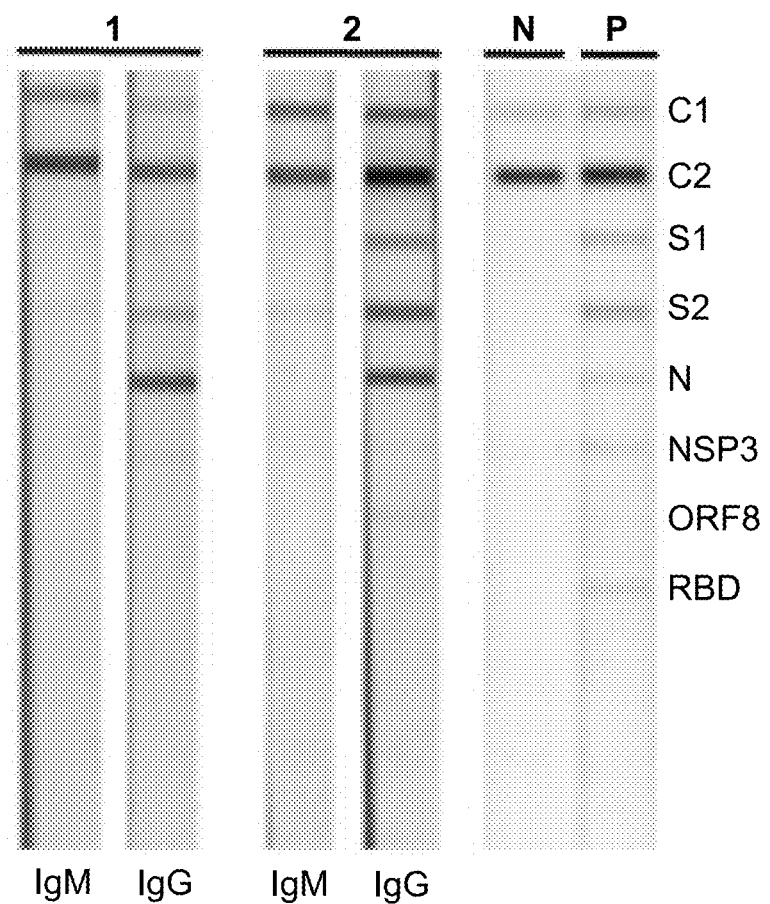
FIG. 2 provides a photomicrographic image of SARS-CoV-2 IgG and IgM immunoblots (IBs) with sera from two patients (1 and 2) and positive (P) and negative (N) control human sera. The positive control (P) was pooled sera from patients positive for SARS-CoV-2 by real-time RT-PCR, and showed reactivity with S1, S2, N, NSP3/ORF1A, ORF8, and RBD polypeptides in both IgG and IgM IBs. The negative control (N) was pooled human sera from patients prior to August, 2019, and did not react with the four SARS-CoV-2 antigens. C1, mixture of purified IgM and purified IgG; C2, Protein L. The positions of S1, S2, N, NSP3/ORF1A, ORF8, and RBD proteins in the membrane strips are also indicated.

SARS-CoV-2 IBs with S1, S2, RBD, N, NSP3, and ORF8 target antigens showed at least equivalent sensitivity and specificity to the four-protein IBs used in Example 1. FIG. 2 shows representative blots from patient sera from patients positive for SARS-CoV-2 by real-time RT-PCR. For Patient 1 (1), IgM IB results were negative, and IgG results were positive (S1, S2, N, and NSP bands were observed). For Patient 2 (2), IgM results were indeterminate (only S2 band observed), and IgG results were positive (S1, S2, N, and ORF8 bands were observed).

Example 3. ImmunoBlot Testing with IgA

ImmunoBlot testing is performed as described above in Examples 1 and 2, but binding of IgA antibodies to the target antigens is detected with anti-human IgA antisera. Recognition of any two of the target antigens, S1, S2, RBD, N, NSP3, and ORF8 is scored as an overall positive reaction for IgA antibodies.

What is claimed is:

1. A composition comprising at least four labelled and/or tagged and/or bound amino acid sequences, wherein the at least four labelled and/or tagged and/or bound amino acid sequences comprise amino acid sequences SEQ ID NO: 1, SEQ ID NO: 2, SEQ ID NO: 3, and SEQ ID NO: 4, and variants thereof which retain the immunological binding profile of the corresponding non-variant.

2. The composition of claim 1, wherein the at least four labelled and/or tagged and/or bound amino acid sequences are bound to a substance selected from the group consisting of nitrocellulose, nylon, polyvinylidene difluoride (PVDF), magnetic beads, metal, plastic and agarose.

3. The composition of claim 1, further comprising at least two labelled and/or tagged and/or bound amino acid sequences, wherein the at least two labelled and/or tagged and/or bound amino acid sequences comprise amino acid sequences SEQ ID NO: 5 and SEQ ID NO: 6, and variants thereof which retain the immunological binding profile of the corresponding non-variant.

4. A method for detecting IgM-class or IgA-class antibodies resulting from infection by a coronavirus, if present in a biological sample obtained from a subject suspected of having a coronavirus infection, the method comprising:

a) providing a composition comprising at least four labelled and/or tagged and/or bound amino acid sequences, wherein the at least four labelled and/or tagged and/or bound amino acid sequences comprise amino acid sequences SEQ ID NO: 1, SEQ ID NO: 2, SEQ ID NO: 3, and SEQ ID NO: 4, and variants thereof which retain the immunological binding profile of the corresponding non-variant;

b) providing the biological sample obtained from the subject suspected of having a coronavirus infection;

c) contacting the biological sample with the composition of step a) under conditions appropriate for specific antibody binding to an epitope; and d) detecting specific binding of IgM-class or IgA-class antibodies with the amino acid sequences of step a), wherein the sample is scored as positive for coronavirus infection when at least two of the amino acid sequences of step a) exhibit positive binding with IgM-class or IgA-class antibodies from the biological sample.

5. The method of claim 4 wherein the binding of IgM-class or IgA-class antibodies is detected through the use of an anti-human IgM antibody or an anti-human IgA-antibody linked to a detectable moiety.

6. The method of claim 4 wherein the amino acid sequences of step a) further comprise amino acid sequences SEQ ID NO: 5 and SEQ ID NO: 6 and variants thereof which retain the immunological binding profile of the corresponding non-variant; and wherein the sample is scored as positive for coronavirus infection when at least two of the amino acid sequences of step a) exhibit positive binding with IgM-class or IgA-class antibodies from the biological sample.

7. The method of claim 6 wherein the binding of IgM-class or IgA-class antibodies is detected through the use of an anti-human IgM antibody and/or an anti-human IgA-antibody linked to a detectable moiety.

8. The method of claim 5, wherein the detectable moiety is selected from the group consisting of chromophores, radioactive moieties, and enzymes.

9. The method of claim 8, wherein the detectable moiety comprises alkaline phosphatase.

10. The method of claim 8, wherein the detectable moiety comprises biotin.

11. A method for detecting IgG-class antibodies resulting from infection by a coronavirus, if present in a biological sample obtained from a subject suspected of having a coronavirus infection, the method comprising:
  a) providing a composition comprising at least four labelled and/or tagged and/or bound amino acid sequences, wherein the at least four labelled and/or tagged and/or bound amino acid sequences comprise amino acid sequences SEQ ID NO: 1, SEQ ID NO: 2, SEQ ID NO: 3, and SEQ ID NO: 4, and variants thereof which retain the immunological binding profile of the corresponding non-variant;
  b) providing the biological sample obtained from the subject suspected of having a coronavirus infection;
  c) contacting the biological sample with the composition of step a) under conditions appropriate for specific antibody binding to an epitope; and
  d) detecting specific binding of IgG-class antibodies with the amino acid sequences of step a), wherein the sample is scored as positive for coronavirus infection when positive binding is detected for: SEQ ID NO: 1 or SEQ ID NO: 3 and SEQ ID NO: 4; SEQ ID NO: 1 or SEQ ID NO: 3 and SEQ ID NO: 2; or SEQ ID NO: 2 and SEQ ID NO: 4.

12. The method of claim 11 wherein the binding of IgG-class antibodies is detected through the use of an anti-human IgG antibody linked to a detectable moiety.

13. The method of claim 11 wherein the amino acid sequences of step a) further comprise amino acid sequences SEQ ID NO: 5 and SEQ ID NO: 6 and variants thereof which retain the immunological binding profile of the corresponding non-variant; and wherein the sample is scored as positive for coronavirus infection when positive binding with IgG-class antibodies is detected for: SEQ ID NO: 1 or SEQ ID NO: 3 and SEQ ID NO: 2; SEQ ID NO: 1 or SEQ ID NO: 3 and SEQ ID NO: 4; SEQ ID NO: 1 or SEQ ID NO: 3 and SEQ ID NO: 5; SEQ ID NO: 1 or SEQ ID NO: 3 and SEQ ID NO: 6; SEQ ID NO: 2 and SEQ ID NO: 4; SEQ ID NO: 2 and SEQ ID NO: 5; SEQ ID NO: 2 and SEQ ID NO: 6; SEQ ID NO: 4 and SEQ ID NO: 5; SEQ ID NO: 4 and SEQ ID NO: 6; or SEQ ID NO: 5 and SEQ ID NO: 6.

14. The method of claim 13 wherein the binding of IgG-class antibodies is detected through the use of an anti-human IgG antibody linked to a detectable moiety.

15. The method of claim 12, wherein the detectable moiety is selected from the group consisting of chromophores, radioactive moieties, and enzymes.

16. The method of claim 14, wherein the detectable moiety comprises alkaline phosphatase.

17. The method of claim 14, wherein the detectable moiety comprises biotin.

* * * * *

SEQUENCE LISTING

```
<160> NUMBER OF SEQ ID NOS: 6

<210> SEQ ID NO 1
<211> LENGTH: 850
<212> TYPE: PRT
<213> ORGANISM: SARS-CoV-2

<400> SEQUENCE: 1

Arg Thr Gln Leu Pro Pro Ala Tyr Thr Asn Ser Phe Thr Arg Gly Val
1               5                   10                  15

Tyr Tyr Pro Asp Lys Val Phe Arg Ser Ser Val Leu His Ser Thr Gln
            20                  25                  30

Asp Leu Phe Leu Pro Phe Phe Ser Asn Val Thr Trp Phe His Ala Ile
        35                  40                  45

His Val Ser Gly Thr Asn Gly Thr Lys Arg Phe Asp Asn Pro Val Leu
    50                  55                  60

Pro Phe Asn Asp Gly Val Tyr Phe Ala Ser Thr Glu Lys Ser Asn Ile
65                  70                  75                  80

Ile Arg Gly Trp Ile Phe Gly Thr Thr Leu Asp Ser Lys Thr Gln Ser
                85                  90                  95

Leu Leu Ile Val Asn Asn Ala Thr Asn Val Val Ile Lys Val Cys Glu
            100                 105                 110

Phe Gln Phe Cys Asn Asp Pro Phe Leu Gly Val Tyr Tyr His Lys Asn
        115                 120                 125

Asn Lys Ser Trp Met Glu Ser Glu Phe Arg Val Tyr Ser Ser Ala Asn
    130                 135                 140

Asn Cys Thr Phe Glu Tyr Val Ser Gln Pro Phe Leu Met Asp Leu Glu
145                 150                 155                 160

Gly Lys Gln Gly Asn Phe Lys Asn Leu Arg Glu Phe Val Phe Lys Asn
                165                 170                 175

Ile Asp Gly Tyr Phe Lys Ile Tyr Ser Lys His Thr Pro Ile Asn Leu
            180                 185                 190

Val Arg Asp Leu Pro Gln Gly Phe Ser Ala Leu Glu Pro Leu Val Asp
        195                 200                 205

Leu Pro Ile Gly Ile Asn Ile Thr Arg Phe Gln Thr Leu Leu Ala Leu
    210                 215                 220

His Arg Ser Tyr Leu Thr Pro Gly Asp Ser Ser Ser Gly Trp Thr Ala
225                 230                 235                 240

Gly Ala Ala Ala Tyr Tyr Val Gly Tyr Leu Gln Pro Arg Thr Phe Leu
                245                 250                 255
```

```
Leu Lys Tyr Asn Glu Asn Gly Thr Ile Thr Asp Ala Val Asp Cys Ala
        260                 265                 270

Leu Asp Pro Leu Ser Glu Thr Lys Cys Thr Leu Lys Ser Phe Thr Val
        275                 280                 285

Glu Lys Gly Ile Tyr Gln Thr Ser Asn Phe Arg Val Gln Pro Thr Glu
        290                 295                 300

Ser Ile Val Arg Phe Pro Asn Ile Thr Asn Leu Cys Pro Phe Gly Glu
305                 310                 315                 320

Val Phe Asn Ala Thr Arg Phe Ala Ser Val Tyr Ala Trp Asn Arg Lys
                325                 330                 335

Arg Ile Ser Asn Cys Val Ala Asp Tyr Ser Val Leu Tyr Asn Ser Ala
            340                 345                 350

Ser Phe Ser Thr Phe Lys Cys Tyr Gly Val Ser Pro Thr Lys Leu Asn
        355                 360                 365

Asp Leu Cys Phe Thr Asn Val Tyr Ala Asp Ser Phe Val Ile Arg Gly
370                 375                 380

Asp Glu Val Arg Gln Ile Ala Pro Gly Gln Thr Gly Lys Ile Ala Asp
385                 390                 395                 400

Tyr Asn Tyr Lys Leu Pro Asp Asp Phe Thr Gly Cys Val Ile Ala Trp
                405                 410                 415

Asn Ser Asn Asn Leu Asp Ser Lys Val Gly Gly Asn Tyr Asn Tyr Leu
            420                 425                 430

Tyr Arg Leu Phe Arg Lys Ser Asn Leu Lys Pro Phe Glu Arg Asp Ile
        435                 440                 445

Ser Thr Glu Ile Tyr Gln Ala Gly Ser Thr Pro Cys Asn Gly Val Glu
    450                 455                 460

Gly Phe Asn Cys Tyr Phe Pro Leu Gln Ser Tyr Gly Phe Gln Pro Thr
465                 470                 475                 480

Asn Gly Val Gly Tyr Gln Pro Tyr Arg Val Val Val Leu Ser Phe Glu
                485                 490                 495

Leu Leu His Ala Pro Ala Thr Val Cys Gly Pro Lys Lys Ser Thr Asn
            500                 505                 510

Leu Val Lys Asn Lys Cys Val Asn Phe Asn Phe Asn Gly Leu Thr Gly
        515                 520                 525

Thr Gly Val Leu Thr Glu Ser Asn Lys Lys Phe Leu Pro Phe Gln Gln
    530                 535                 540

Phe Gly Arg Asp Ile Ala Asp Thr Thr Asp Ala Val Arg Asp Pro Gln
545                 550                 555                 560

Thr Leu Glu Ile Leu Asp Ile Thr Pro Cys Ser Phe Gly Gly Val Ser
                565                 570                 575

Val Ile Thr Pro Gly Thr Asn Thr Ser Asn Gln Val Ala Val Leu Tyr
            580                 585                 590

Gln Asp Val Asn Cys Thr Glu Val Pro Val Ala Ile His Ala Asp Gln
        595                 600                 605

Leu Thr Pro Thr Trp Arg Val Tyr Ser Thr Gly Ser Asn Val Phe Gln
    610                 615                 620

Thr Arg Ala Gly Cys Leu Ile Gly Ala Glu His Val Asn Asn Ser Tyr
625                 630                 635                 640

Glu Cys Asp Ile Pro Ile Gly Ala Gly Ile Cys Ala Ser Tyr Gln Thr
                645                 650                 655

Gln Thr Asn Ser Pro Arg Arg Ala Arg Ser Val Ala Ser Gln Ser Ile
            660                 665                 670

Ile Ala Tyr Thr Met Ser Leu Gly Ala Glu Asn Ser Val Ala Tyr Ser
```

-continued

```
        675                 680                 685

Asn Asn Ser Ile Ala Ile Pro Thr Asn Phe Thr Ile Ser Val Thr Thr
    690                 695                 700

Glu Ile Leu Pro Val Ser Met Thr Lys Thr Ser Val Asp Cys Thr Met
705                 710                 715                 720

Tyr Ile Cys Gly Asp Ser Thr Glu Cys Ser Asn Leu Leu Leu Gln Tyr
                725                 730                 735

Gly Ser Phe Cys Thr Gln Leu Asn Arg Ala Leu Thr Gly Ile Ala Val
            740                 745                 750

Glu Gln Asp Lys Asn Thr Gln Glu Val Phe Ala Gln Val Lys Gln Ile
        755                 760                 765

Tyr Lys Thr Pro Pro Ile Lys Asp Phe Gly Gly Phe Asn Phe Ser Gln
    770                 775                 780

Ile Leu Pro Asp Pro Ser Lys Pro Ser Lys Arg Ser Phe Ile Glu Asp
785                 790                 795                 800

Leu Leu Phe Asn Lys Val Thr Leu Ala Asp Ala Gly Phe Ile Lys Gln
                805                 810                 815

Tyr Gly Asp Cys Leu Gly Asp Ile Ala Ala Arg Asp Leu Ile Cys Ala
            820                 825                 830

Gln Lys Phe Asn Gly Leu Thr Val Leu Pro Pro Leu Leu Thr Asp Glu
        835                 840                 845

Met Ile
    850

<210> SEQ ID NO 2
<211> LENGTH: 221
<212> TYPE: PRT
<213> ORGANISM: SARS-CoV-2

<400> SEQUENCE: 2

Val Gln Pro Thr Glu Ser Ile Val Arg Phe Pro Asn Ile Thr Asn Leu
1               5                   10                  15

Cys Pro Phe Gly Glu Val Phe Asn Ala Thr Arg Phe Ala Ser Val Tyr
            20                  25                  30

Ala Trp Asn Arg Lys Arg Ile Ser Asn Cys Val Ala Asp Tyr Ser Val
        35                  40                  45

Leu Tyr Asn Ser Ala Ser Phe Ser Thr Phe Lys Cys Tyr Gly Val Ser
    50                  55                  60

Pro Thr Lys Leu Asn Asp Leu Cys Phe Thr Asn Val Tyr Ala Asp Ser
65                  70                  75                  80

Phe Val Ile Arg Gly Asp Glu Val Arg Gln Ile Ala Pro Gly Gln Thr
                85                  90                  95

Gly Lys Ile Ala Asp Tyr Asn Tyr Lys Leu Pro Asp Asp Phe Thr Gly
            100                 105                 110

Cys Val Ile Ala Trp Asn Ser Asn Asn Leu Asp Ser Lys Val Gly Gly
        115                 120                 125

Asn Tyr Asn Tyr Leu Tyr Arg Leu Phe Arg Lys Ser Asn Leu Lys Pro
    130                 135                 140

Phe Glu Arg Asp Ile Ser Thr Glu Ile Tyr Gln Ala Gly Ser Thr Pro
145                 150                 155                 160

Cys Asn Gly Val Glu Gly Phe Asn Cys Tyr Phe Pro Leu Gln Ser Tyr
                165                 170                 175

Gly Phe Gln Pro Thr Asn Gly Val Gly Tyr Gln Pro Tyr Arg Val Val
            180                 185                 190
```

-continued

Val Leu Ser Phe Glu Leu Leu His Ala Pro Ala Thr Val Cys Gly Pro
        195                 200                 205

Lys Lys Ser Thr Asn Leu Val Lys Asn Lys Cys Val Asn
    210                 215                 220

<210> SEQ ID NO 3
<211> LENGTH: 443
<212> TYPE: PRT
<213> ORGANISM: SARS-CoV-2

<400> SEQUENCE: 3

Ser Leu Gly Ala Glu Asn Ser Val Ala Tyr Ser Asn Asn Ser Ile Ala
1               5                   10                  15

Ile Pro Thr Asn Phe Thr Ile Val Phe Ala Gln Val Lys Gln Ile Tyr
            20                  25                  30

Lys Thr Pro Pro Ile Lys Asp Phe Gly Gly Phe Asn Phe Ser Gln Ile
        35                  40                  45

Leu Pro Asp Pro Ser Lys Pro Ser Lys Arg Ser Phe Ile Glu Asp Leu
    50                  55                  60

Leu Phe Asn Lys Val Thr Leu Ala Asp Ala Gly Phe Ile Lys Gln Tyr
65                  70                  75                  80

Gly Asp Cys Leu Gly Asp Ile Ala Ala Arg Asp Leu Ile Cys Ala Gln
                85                  90                  95

Lys Phe Asn Gly Leu Thr Val Leu Pro Pro Leu Leu Thr Asp Glu Met
            100                 105                 110

Ile Ala Gln Tyr Thr Ser Ala Leu Leu Ala Gly Thr Ile Thr Ser Gly
        115                 120                 125

Trp Thr Phe Gly Ala Gly Ala Ala Leu Gln Ile Pro Phe Ala Met Gln
    130                 135                 140

Met Ala Tyr Arg Phe Asn Gly Ile Gly Val Thr Gln Asn Val Leu Tyr
145                 150                 155                 160

Glu Asn Gln Lys Leu Ile Ala Asn Gln Phe Asn Ser Ala Ile Gly Lys
                165                 170                 175

Ile Gln Asp Ser Leu Ser Ser Thr Ala Ser Ala Leu Gly Lys Leu Gln
            180                 185                 190

Asp Val Val Asn Gln Asn Ala Gln Ala Leu Asn Thr Leu Val Lys Gln
        195                 200                 205

Leu Ser Ser Asn Phe Gly Ala Ile Ser Ser Val Leu Asn Asp Ile Leu
    210                 215                 220

Ser Arg Leu Asp Lys Val Glu Ala Glu Val Gln Ile Asp Arg Leu Ile
225                 230                 235                 240

Thr Gly Arg Leu Gln Ser Leu Gln Thr Tyr Val Thr Gln Gln Leu Ile
                245                 250                 255

Arg Ala Ala Glu Ile Arg Ala Ser Ala Asn Leu Ala Ala Thr Lys Met
            260                 265                 270

Ser Glu Cys Val Leu Gly Gln Ser Lys Arg Val Asp Phe Cys Gly Lys
        275                 280                 285

Gly Tyr His Leu Met Ser Phe Pro Gln Ser Ala Pro His Gly Val Val
    290                 295                 300

Phe Leu His Val Thr Tyr Val Pro Ala Gln Glu Lys Asn Phe Thr Thr
305                 310                 315                 320

Ala Pro Ala Ile Cys His Asp Gly Lys Ala His Phe Pro Arg Glu Gly
                325                 330                 335

Val Phe Val Ser Asn Gly Thr His Trp Phe Val Thr Gln Arg Asn Phe
            340                 345                 350

Tyr Glu Pro Gln Ile Ile Thr Thr Asp Asn Thr Phe Val Ser Gly Asn
            355                 360                 365

Cys Asp Val Val Ile Gly Ile Val Asn Asn Thr Val Tyr Asp Pro Leu
            370                 375                 380

Gln Pro Glu Leu Asp Ser Phe Lys Glu Leu Asp Lys Tyr Phe Lys
385                 390                 395                 400

Asn His Thr Ser Pro Asp Val Asp Leu Gly Asp Ile Ser Gly Ile Asn
            405                 410                 415

Ala Ser Val Val Asn Ile Gln Lys Glu Ile Asp Arg Leu Asn Glu Val
            420                 425                 430

Ala Lys Asn Leu Asn Glu Ser Leu Ile Asp Leu
            435                 440

<210> SEQ ID NO 4
<211> LENGTH: 419
<212> TYPE: PRT
<213> ORGANISM: SARS-CoV-2

<400> SEQUENCE: 4

Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
            20                  25                  30

Ser Gly Ala Arg Ser Lys Gln Arg Arg Pro Gln Gly Leu Pro Asn Asn
            35                  40                  45

Thr Ala Ser Trp Phe Thr Ala Leu Thr Gln His Gly Lys Glu Asp Leu
50                  55                  60

Lys Phe Pro Arg Gly Gln Gly Val Pro Ile Asn Thr Asn Ser Ser Pro
65                  70                  75                  80

Asp Asp Gln Ile Gly Tyr Tyr Arg Arg Ala Thr Arg Arg Ile Arg Gly
            85                  90                  95

Gly Asp Gly Lys Met Lys Asp Leu Ser Pro Arg Trp Tyr Phe Tyr Tyr
            100                 105                 110

Leu Gly Thr Gly Pro Glu Ala Gly Leu Pro Tyr Gly Ala Asn Lys Asp
            115                 120                 125

Gly Ile Ile Trp Val Ala Thr Glu Gly Ala Leu Asn Thr Pro Lys Asp
130                 135                 140

His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
            165                 170                 175

Arg Gly Gly Ser Gln Ala Ser Ser Arg Ser Ser Ser Arg Ser Arg Asn
            180                 185                 190

Ser Ser Arg Asn Ser Thr Pro Gly Ser Ser Arg Gly Thr Ser Pro Ala
            195                 200                 205

Arg Met Ala Gly Asn Gly Gly Asp Ala Ala Leu Ala Leu Leu Leu Leu
            210                 215                 220

Asp Arg Leu Asn Gln Leu Glu Ser Lys Met Ser Gly Lys Gly Gln Gln
225                 230                 235                 240

Gln Gln Gly Gln Thr Val Thr Lys Lys Ser Ala Ala Glu Ala Ser Lys
            245                 250                 255

Lys Pro Arg Gln Lys Arg Thr Ala Thr Lys Ala Tyr Asn Val Thr Gln
            260                 265                 270

Ala Phe Gly Arg Arg Gly Pro Glu Gln Thr Gln Gly Asn Phe Gly Asp

```
                       275                 280                 285
    Gln Glu Leu Ile Arg Gln Gly Thr Asp Tyr Lys His Trp Pro Gln Ile
        290                 295                 300
    Ala Gln Phe Ala Pro Ser Ala Ser Ala Phe Phe Gly Met Ser Arg Ile
    305                 310                 315                 320
    Gly Met Glu Val Thr Pro Ser Gly Thr Trp Leu Thr Tyr Thr Gly Ala
                    325                 330                 335
    Ile Lys Leu Asp Asp Lys Asp Pro Asn Phe Lys Asp Gln Val Ile Leu
                340                 345                 350
    Leu Asn Lys His Ile Asp Ala Tyr Lys Thr Phe Pro Pro Thr Glu Pro
                355                 360                 365
    Lys Lys Asp Lys Lys Lys Lys Ala Asp Glu Thr Gln Ala Leu Pro Gln
        370                 375                 380
    Arg Gln Lys Lys Gln Gln Thr Val Thr Leu Leu Pro Ala Ala Asp Leu
    385                 390                 395                 400
    Asp Asp Phe Ser Lys Gln Leu Gln Gln Ser Met Ser Ser Ala Asp Ser
                    405                 410                 415
    Thr Gln Ala

<210> SEQ ID NO 5
<211> LENGTH: 315
<212> TYPE: PRT
<213> ORGANISM: SARS-CoV-2

<400> SEQUENCE: 5

Glu Val Arg Thr Ile Lys Val Phe Thr Thr Val Asp Asn Ile Asn Leu
    1               5                   10                  15
    His Thr Gln Val Val Asp Met Ser Met Thr Tyr Gly Gln Gln Phe Gly
                    20                  25                  30
    Pro Thr Tyr Leu Asp Gly Ala Asp Val Thr Lys Ile Lys Pro His Asn
                35                  40                  45
    Ser His Glu Gly Lys Thr Phe Tyr Val Leu Pro Asn Asp Asp Thr Leu
        50                  55                  60
    Arg Val Glu Ala Phe Glu Tyr Tyr His Thr Thr Asp Pro Ser Phe Leu
    65                  70                  75                  80
    Gly Arg Tyr Met Ser Ala Leu Asn His Thr Lys Lys Trp Lys Tyr Pro
                    85                  90                  95
    Gln Val Asn Gly Leu Thr Ser Ile Lys Trp Ala Asp Asn Asn Cys Tyr
                    100                 105                 110
    Leu Ala Thr Ala Leu Leu Thr Leu Gln Gln Ile Glu Leu Lys Phe Asn
                115                 120                 125
    Pro Pro Ala Leu Gln Asp Ala Tyr Tyr Arg Ala Arg Ala Gly Glu Ala
                130                 135                 140
    Ala Asn Phe Cys Ala Leu Ile Leu Ala Tyr Cys Asn Lys Thr Val Gly
    145                 150                 155                 160
    Glu Leu Gly Asp Val Arg Glu Thr Met Ser Tyr Leu Phe Gln His Ala
                    165                 170                 175
    Asn Leu Asp Ser Cys Lys Arg Val Leu Asn Val Val Cys Lys Thr Cys
                    180                 185                 190
    Gly Gln Gln Gln Thr Thr Leu Lys Gly Val Glu Ala Val Met Tyr Met
                195                 200                 205
    Gly Thr Leu Ser Tyr Glu Gln Phe Lys Lys Gly Val Gln Ile Pro Cys
                210                 215                 220
    Thr Cys Gly Lys Gln Ala Thr Lys Tyr Leu Val Gln Gln Glu Ser Pro
```

-continued

```
                225                 230                 235                 240

Phe Val Met Met Ser Ala Pro Pro Ala Gln Tyr Glu Leu Lys His Gly
                245                 250                 255

Thr Phe Thr Cys Ala Ser Glu Tyr Thr Gly Asn Tyr Gln Cys Gly His
                260                 265                 270

Tyr Lys His Ile Thr Ser Lys Glu Thr Leu Tyr Cys Ile Asp Gly Ala
                275                 280                 285

Leu Leu Thr Lys Ser Ser Glu Tyr Lys Gly Pro Ile Thr Asp Val Phe
                290                 295                 300

Tyr Lys Glu Asn Ser Tyr Thr Thr Thr Ile Lys
305                 310                 315

<210> SEQ ID NO 6
<211> LENGTH: 121
<212> TYPE: PRT
<213> ORGANISM: SARS-CoV-2

<400> SEQUENCE: 6

Met Lys Phe Leu Val Phe Leu Gly Ile Ile Thr Thr Val Ala Ala Phe
1               5                   10                  15

His Gln Glu Cys Ser Leu Gln Ser Cys Thr Gln His Gln Pro Tyr Val
                20                  25                  30

Val Asp Asp Pro Cys Pro Ile His Phe Tyr Ser Lys Trp Tyr Ile Arg
            35                  40                  45

Val Gly Ala Arg Lys Ser Ala Pro Leu Ile Glu Leu Cys Val Asp Glu
        50                  55                  60

Ala Gly Ser Lys Ser Pro Ile Gln Tyr Ile Asp Ile Gly Asn Tyr Thr
65                  70                  75                  80

Val Ser Cys Leu Pro Phe Thr Ile Asn Cys Gln Glu Pro Lys Leu Gly
                85                  90                  95

Ser Leu Val Val Arg Cys Ser Phe Tyr Glu Asp Phe Leu Glu Tyr His
                100                 105                 110

Asp Val Arg Val Val Leu Asp Phe Ile
                115                 120
```